US006989155B1

(12) United States Patent
Ganderton et al.

(10) Patent No.: US 6,989,155 B1
(45) Date of Patent: Jan. 24, 2006

(54) POWDERS

(75) Inventors: David Ganderton, Exeter (GB); David Alexander Vodden Morton, Bath (GB); Paul Lucas, Deal (GB)

(73) Assignee: Vectura Limited, Wiltshire (GB)

( * ) Notice: Subject to any disclaimer, the term of this patent is extended or adjusted under 35 U.S.C. 154(b) by 0 days.

(21) Appl. No.: 09/857,392

(22) PCT Filed: Dec. 9, 1999

(86) PCT No.: PCT/GB99/04156

§ 371 (c)(1),
(2), (4) Date: Dec. 7, 2001

(87) PCT Pub. No.: WO00/33811

PCT Pub. Date: Jun. 15, 2000

(30) Foreign Application Priority Data

Dec. 9, 1998 (GB) .................................... 9827145

(51) Int. Cl.
 *A61K 9/14* (2006.01)
 *A61K 9/50* (2006.01)
 *B32B 15/02* (2006.01)
(52) U.S. Cl. ........................ 424/499; 424/489; 428/402
(58) Field of Classification Search ................ 424/489, 424/499; 264/4.6; 428/402
See application file for complete search history.

(56) References Cited

U.S. PATENT DOCUMENTS 6,518,239 B1 * 2/2003 Kuo et al. ..................... 514/2

FOREIGN PATENT DOCUMENTS

| WO | 9623485 | 8/1996 |
| WO | 9632096 | 10/1996 |
| WO | WO 96/32096 | * 10/1996 |
| WO | 9703649 | 2/1997 |

OTHER PUBLICATIONS

Jean W. Tom and Pablo G. Debenedetti; Particle Formatton with Supercritical Fluids—A Review; *J. Aerosol Sci.*, vol. 22, No. 5 pp. 555-584, 1991.
D.A.V. Morton; Aerosol Processing Methods Leading to Enchanced Powder Products; Extract from: Proceedings of the Aerosol Society Tenth Annual Conference, Swansea, 1996; Plenary Lecture.
Edwards, et al.; Large Porous Particies for Pulmonary Drug Delivery; *Science*, vol. 276, Jun. 20, 1997; pp. 1868-1871.
Yamashita et al.; A Novel Formulation of Dry Powder for Inhalation of Peptides and Proteins; *Respiratory Drug Delivery*, VI, 1998; pp. 483-485.
G. Röschelsen et al.; Preparation and Optimization of L-leucine as Lubricant for Effervescent Tablet Formulations; *Pharmaceutica Acta Helvetiae* 70 (1995); pp. 133-139.
International Search Report; PCT/GB99/04156; Jun. 28, 2000.

* cited by examiner

*Primary Examiner*—Carlos A. Azpuru
(74) *Attorney, Agent, or Firm*—Davidson, Davidson & Kappel, LLC

(57) ABSTRACT

Particles of an amino acid such as leucine may be formed from an amino acid vapor, for example by aerosol condensation, or by spray drying. The amino acid particles have a bulk density of not more than 0.1 $gcm^{-3}$ or have a mass median aerodynamic diameter of not more than 10 $\mu$m or are in the form of flakes having a thickness of not more than 100 $\mu$m. The inclusion of the particles of amino acid in powder for use in dry powder inhalers has been found to improve the respirable fraction of the active material in the powder.

26 Claims, No Drawings

POWDERS

This application is a U.S. National Phase application under 35 U.S.C. § 371 based on PCT Application No. PCT/GB99/04156, which claims priority to Great Britain Application No. 9827145.5.

This invention relates to particles for use in powders. In particular, but not exclusively, the invention relates to particles for use in powder compositions for dry powder inhalers, especially particles of an amino acid for use in such powders.

Inhalers are well known devices for administering pharmaceutical products to the respiratory tract by inhalation. Inhalers are widely used particularly in the treatment of diseases of the respiratory tract.

There are a number of types of inhaler currently available. One device is the dry powder inhaler. The delivery of dry powder particles of pharmaceutical products to the respiratory tract presents certain problems. The inhaler should deliver the maximum possible proportion of the active particles expelled to the lungs, including a significant proportion to the lower lung, preferably at the low inhalation capabilities to which some patients, especially asthmatics, are limited. It has been found however, that, when currently available dry powder inhaler devices are used, in many cases only about 10% of the active particles that leave the device on inhalation are deposited in the lower lung. More efficient dry powder inhalers would give clinical benefits.

The physical properties of the powder used in the inhaler affect both the efficiency and reproducibility of delivery of the active particles and the site of deposition in the respiratory tract.

On exit from the inhaler device, the active particles should form a physically and chemically stable aerocolloid which remains in suspension until it reaches a conducting bronchiole of smaller branching of the pulmonary tree or other absorption site preferably in the lower lung. Once at the absorption site, the active particle should be capable of efficient collection by the pulmonary mucosa with no active particles being exhaled from the absorption site.

The size of the active particles is particularly important. For effective delivery of active particles deep into the lungs, the active particles should be small, with an equivalent aerodynamic diameter substantially in the range of 0.1 to 5 $\mu$m, approximately spherical and monodispersed in the respiratory tract. Small particles are, however, thermodynamically unstable due to their high surface area to volume ratio, which provides significant excess surface free energy and encourages particles to agglomerate. In the inhaler, agglomeration of small particles and adherence of particles to the walls of the inhaler are problems that result in the active particles leaving the inhaler as large stable agglomerates or being unable to leave the inhaler and remaining adhered to the interior of the inhaler.

The uncertainty as to the extent of formation of stable agglomerates of the particles between each actuation of the inhaler and also between different inhalers and different batches of particles leads to poor dose reproducibility.

Some known dry powders for use in dry powder inhalers include carrier particles to which the fine active particles adhere whilst in the inhaler device, but which are dispersed from the surfaces of the carrier particles on inhalation into the respiratory tract to give a fine suspension. The carrier particles are often large particles greater than 90 $\mu$m in diameter to give good flow properties as indicated above. Small particles with a diameter of less than 10 $\mu$m may be deposited on the wall of the delivery device and have poor flow and entrainment properties leading to poor dose uniformity.

The increased efficiency of redispersion of the fine active particles from the agglomerates or from the surfaces of carrier particles during inhalation is regarded as a critical step in improving the efficiency of the dry powder inhalers.

In some dry powder inhaler devices, doses of powder containing only active particles are dispensed. The powder contains no carrier particles or other additives and the amount of powder in each dose is small, usually less than 1 mg. The volume of the dose may be, for example, approximately 6.5 $\mu$l.

Problems involved in dispensing a powder containing only particles of active material include i. formation of stable agglomerates of the small particles which often are not broken down into individual particles in the air stream when the particles are inhaled and are, therefore, less likely to reach the lower lung on inhalation of the powder than the fine individual active particles;

ii. variation in the amount of powder metered from a reservoir of the inhalation device due to poor flow properties of the powder and inconsistent agglomeration, leading to inconsistency in the size of dose, which may vary as much as ±50% compared with the nominal dose for the device;

iii. incomplete removal of the dose from the device due to adherence of the particles to the walls of the device, leading to poor dose reproducibility.

In order to increase the proportion of active particles which may be delivered to the lung, it has been proposed to add a further component to the powder.

WO96/23485 describes the addition of an additive material to a powder for inhalation including carrier particles and active particles to improve the respirable fraction of the active material. A preferred additive material is leucine.

WO97/03649 also describes the addition of leucine to powder compositions for dry powder inhalers, in which the compositions do not include carrier particles.

While the addition of the additive material to the compositions described in WO96/23485 and WO97/03649 give improved respirable fractions of the active components, it would clearly be desirable to make the effect of the additive material still more beneficial.

According to the invention there are provided amino acid particles in which a sample of the particles has a bulk density not more than 0.1 gcm$^3$.

The bulk density of the sample may be determined using the test described below.

The amino acid particles may comprise one amino acid or a mixture of two or more amino acids. Preferred amino acids include those amino acids which sublime, in particular leucine and iso-leucine, and also alanine, valine, serine and phenyl alanine.

An especially preferred amino acid is leucine.

The bulk density of standard crystalline leucine currently available is in the range of 0.6 to 0.7 gcm$^{-3}$ and the bulk density of leucine that has been milled is in the range of 0.3 to 0.4 gcm$^{-3}$. The leucine in accordance with the invention has very low bulk density. It has been found that leucine having a low-density shows flow enhancing properties when added to powders. In particular, the addition of the low-density leucine to a powder gives improved glidant properties as well as improved anti-adherent properties.

Where reference is made to "density" in this specification, it is to be understood as being a reference to bulk density unless it is clear from the context that a different measurement of density is being referred to.

Advantageously, the amino acid particles have a bulk density not more than 0.1 gcm$^{-3}$ and preferably not more than 0.05 gcm$^{-3}$.

The invention also provides amino acid powder, the powder having a bulk density of not more than 0.1 gcm$^{-3}$.

A second aspect of the invention provides amino acid particles having a mass median aerodynamic diameter (MMAD) of not more than 5 μm. Reference is made above to the MMAD of the particles. Where the particles have a low bulk density in accordance with the first aspect of the invention, the actual diameter of the particles can be relatively large while the MMAD is still small enough for the desired aerodynamic characteristics of the particles.

Alternatively, the size distribution of the particles can be characterised by their volume mean diameter (VMD). Advantageously, the VMD of the amino acid particles is not more than 10 μm, preferably not more than 5 μm.

As indicated above, it has been found that a particularly preferred amino acid is leucine.

It has been found that leucine having a VMD of less than 10 μm has improved flow properties when added to powders. It is thought that the small particle size of the leucine is closely associated with a low bulk density. As described above, such particles give improved flow properties.

Advantageously, the amino acid particles have a volume mean diameter not more than 5 μm. That size is very small for amino acid particles, in particular leucine particles.

In a third aspect of the invention, there is provided amino acid particles being in the form of flakes having a thickness of not more than 0.5 μm. Preferably the flakes have a thickness of not more than 100 nm.

As indicated above, a preferred amino acid is leucine. Conventional leucine is in the form of flakes having a thickness of at least 1 μm and usually greater than 5 μm. It has been found that, by reducing the thickness of the flakes, the flow properties of the leucine particles is improved. It is thought that when the leucine is added to a powder the thin leucine flakes act as "spacers" between the particles of the powder which improves its flow properties, in particular the glidant properties.

In some cases, the particles of the third aspect of the invention will also have the desired MMAD (or VMD) of the second aspect of the invention.

It has been found that the thin flakes of leucine in accordance with this further aspect of the invention generally have a low density and improved flow properties.

It has been found to be particularly advantageous for the leucine to be in the form of flakes having a thickness of less than about 100 nm.

It has been found that when, for example, the leucine flakes have been prepared using the spray drying method described below, that they have a very small thickness of less than 100 nm and a relatively large width. It has been found that the flakes may become fractured during subsequent processing of the powder but that the beneficial properties of the flakes are not substantially diminished. It is thought, therefore, that it is the very small thickness of the flakes which gives their advantageous properties.

The aspect ratio of the flakes of amino acid can be considered to be the (width of the particles)/(thickness of the particles). Advantageously the aspect ratio of the particles is at least 20, preferably at least 50.

Observation of the thickness of the flakes may be made by studying electron microscope (SEM) images of the particles. For example, flakes may be mounted on an electron microscope stub with double sided tape and coated with gold prior to examination on an electron microscope.

An alternative method for observing the dimensions of particles of the present invention is by sizing the particles on a microscope slide in a similar way to that described in British Pharmacopoeia 1973 (page 645, Ergotamine Aerosol Inhalation). In this case a small quantity of particles, for example 10 to 100 mg, are dropped onto a microscope slide and examined under a microscope to assess the particle size of the deposit.

Where reference is made above to the shape and size of the particles, it should be understood that the reference is to the shape and size of the individual particles. Those particles may become agglomerated to form clusters of individual particles.

The amino acid of the first, second and third aspects of the invention will all be referred to below as "low-density amino acid" for ease of reference. Furthermore, where the amino acid is, for example, leucine, it will be referred to below as "low-density leucine". It should be understood, however, that the amino acid of the second and third aspects of the invention, for example, might not have the bulk density required in respect of the first aspect of the invention.

Where the amino acid is leucine, advantageously, the leucine is L-leucine. L-leucine is a naturally occurring form of leucine and is therefore preferred when the leucine is to be used in pharmaceutical compositions or other compositions that may enter the body.

Advantageously, the particles of low-density amino acid include no further materials other than the amino acid. The particles may include a mixture of more than one amino acid.

According to the invention there is also provided a powder for use in a dry powder inhaler, the powder including active material and low-density amino acid particles.

The low-density amino acid is particularly advantageous for use in a powder for inhalation. There are several conventional additives that are included in powder compositions for inhalation to improve the flow properties of the powder. Many of the flow enhancing additives are, however, undesirable for inhalation because they are not particularly physiologically acceptable, for example silica. Amino acids are bio-compatible and relatively safe for inhalation.

It has been found that the addition of the low-density amino acid to a powder for inhalation can give an improved respirable fraction for the powder and/or improved emptying of the powder from the inhaler device on actuation of the inhaler.

Advantageously, the powder includes not more than 10% by weight of low-density amino acid based on the weight of the powder. For powders for inhalation, where the low density amino acid is added to the powder to improve the dispersal of the active particles, it has been found that while the addition of up to 10% by weight of the low-density amino acid can give improved powder performance, on the addition of about 20% by weight of the low-density amino acid, the benefit was reduced.

Where the low-density amino acid is used as a flow aid, for example in powders other than for use in dry powder inhalers, it has been found that the low-density amino acid can be included in greater amounts without detrimental effects, for example the low-density amino acid may be present at a % by weight of 50%.

As indicated above, in some powders for inhalation, active material comprises substantially all of the powder. In some cases a small amount of additives, for example colorants and flavourings are included. Thus, the powder may include less than 10%, preferably less than 5% by weight of materials other than the active material and the amino acid, based on the weight of the powder. The active material may comprise not less than 60% by weight of the powder.

In other powders for inhalation, the powder includes other diluents, for example carrier particles as described above. Thus, the powder may further include particles of a diluent. The carrier particles may be present in an amount of at least 50%, preferably at least 90%, more preferably at least 95%, by weight based on the weight of the powder.

The diluent may have a particle size such that at least 90% by weight of the diluent particles have a particle size not more than 10 $\mu$m. It has been found that the addition of fine particles of diluent gives improved respirable fraction.

Alternatively, the diluent may have a particle size such that at least 90% by weight of the diluent particles have a particle size not less than 50 $\mu$m. Such particles are equivalent to the carrier particles described above and give improved flow properties to the powder.

It has been found that the addition of low-density amino acid gives improved respirable fraction of active particles when the powder is used in a dry powder inhaler. That is thought to be due to the improved flow properties of the powder leading to improved emptying of the powder from the inhaler device and/or improved dispersion of the active particles on actuation of the inhaler device.

Advantageously, the diluent has a fine particle portion having a particle size such that at least 90% by weight of the particle of the fine particle portion have a particle size not more than 10 $\mu$m and a coarse particle portion having a particle size such that at least 90% by weight of the particles have a particle size not less than 50 $\mu$m.

It will be understood that, unless it is clear to the contrary, the particle size or the diameter of the particles referred to is the aerodynamic diameter of the particles MMAD which may be measured by the method indicated below.

The fine particle portion and coarse particle portion may comprise the same material or different materials. Furthermore, each of the fine particle portion and the coarse particle portion may comprise a mixture of more than one material.

The fine particle portion and the coarse particle portion may be, for example, simply mixed together. However, where the fine particle portion and the coarse particle portion comprise the same material, the diluent is advantageously prepared by treating coarse particles of the diluent to dislodge small fragments from their surfaces. The small fragments form the fine particle portion. Such a treatment may be carried out, for example, by careful milling of the coarse particles. Such treatment of the diluent particles is described, for example in WO96/23485.

The diluent particles may be composed of any pharmacologically inert material or combination of materials which is acceptable for inhalation. Advantageously, the diluent particles are composed of one or more crystalline sugars; the diluent particles may be composed of one or more sugar alcohols or polyols. Preferably, the diluent particles are particles of lactose.

Advantageously, the powder includes not more than 10%, preferably not more than 5% by weight of the fine particle portion based on the weight of the powder. The fine particle portion of the diluent has a particle size that is advantageous for the delivery of the particles of the deep lung. It is generally advantageous for as little as possible of materials other than the active material to be transported to the deep lung.

According to the invention, there is also provided, a dry powder inhaler, the inhaler containing powder as described above.

The present invention also provides a method of preparing particles of amino acid, the method including the step of forming solid amino acid particles from a vapour or from a solvent, the method being such that the particles are formed while being suspended in a gas flow.

As indicated above, a conventional method of preparing amino acid, in particular leucine having a small particle size, is by milling the amino acid. Many amino acids, for example leucine are, however, soft materials and it is difficult to prepare leucine having a very small particle size in that way. Furthermore, the preparation of amino acid, for example leucine, using a milling technique increases the risk that there are contaminants or impurities in the amino acid. Furthermore, controlling the physical properties of powder produced by milling is difficult.

By preparing the amino acid by, for example, condensation from a vapour or by drying droplets of a solvent containing leucine, particles of amino acid having a small particle size can be more easily obtained. Furthermore, greater control of particle size and morphology is possible. The particles are produced in suspended form, reducing the risk of contamination. The particles produced suspended in a gas flow may be easily classified and separated by their aerodynamic properties.

The method of producing particles of the amino acid in accordance with the invention will depend on the physical nature of the amino acid. For example, leucine is an amino acid which sublimes and in one advantageous embodiment of the invention, leucine is condensed from leucine vapour to form the low-density particles according to the invention. Other amino acids decompose on heating. Such amino acids are therefore not suitable to be condensed from their vapour but may, for example, be prepared by spray drying in accordance with a further embodiment of the invention to form low density amino acid.

Advantageously, the amino acid is a material which sublimes.

In one aspect of the invention, the method of producing particles of amino acid includes the step of condensing amino acid vapour to form solid amino acid particles. That method is particularly desirable where the amino acid is to be co-condensed with another material. For example, where the amino acid is to be used in a powder including active material, the amino acid and the active material may be co-condensed together.

Advantageously, the particles of amino acid are formed by aerosol condensation. One amino acid which is particularly suited to preparation by that method is leucine.

Leucine sublimes at a temperature of about 220° C.

The method advantageously includes the steps of a) heating an amino acid so that the amino acid forms amino acid vapour;

b) mixing the amino acid vapour with cool air to form a cloud of condensed amino acid particles; and c) collecting the condensed particles.

Advantageously, the amino acid is passed through a furnace. The furnace may be a tube furnace. The initial amino acid particles are advantageously suspended from a fluidised bed by a flow of air. The material may then be carried in the gas flow into the tube furnace where it forms a vapour.

The condensed particles are advantageously collected in a cyclone and/or a filter or by precipitation.

Advantageously, the method includes the step of heating the amino acid particles to a temperature of at least 150° C. at ambient pressure. It is envisaged that the pressure could be reduced to reduce the temperature required to form the amino acid vapour. The temperature to which the amino acid is heated will depend on the nature of the amino acid used and the temperature required to form a vapour of that amino acid.

According to a further aspect of the invention, in the method of producing particles of amino acid, droplets of amino acid in a solvent are dried in a spray drying step to form solid particles of amino acid, the method being such that at least some of the amino acid sublimes during the spray drying.

Advantageously, the method includes the step of spray drying amino acid in a solvent.

Advantageously, the material to be dried comprises amino acid in solution, which is advantageously an aqueous solution.

Where the amino acid is one which sublimes, for example leucine, it is thought that it may be advantageous for some sublimation of the leucine to take place during the spray drying of the leucine to give the most advantageous morphology of the leucine particles produced. In such a case, advantageously, the spray drying method is such that at least some of the amino acid sublimes during the spray drying.

Conventional spray drying of the amino acid may produce large particles of amino acid which are generally spherical in shape. Where the amino acid is leucine, such particles may have a particle diameter of 40 μm or more. Such leucine particles produced by a spray drying method are described in Pharmaceutica Acta Helvetiae 70(1995) 133–139. Such particles have been found to be undesirable in that they do not give the desired properties for the low-density leucine.

Yamashita et al (Respiratory Drug Delivery J1 1998 p 483) describes the use of spray-dried L-isoleucine particles as a hydrophobic carrier for inhalation. As indicated above, conventional spray drying of an amino acid is thought to produce particles having an undesirable morphology. The conventional spray dried particles would, however, have the properties desired in Yamashita having regard to the consideration of hygroscopicity.

WO 98/31346 describes the spray drying of materials for inhalation. The spray drying is said to diminish the tap density of the material by increasing particle surface irregularities and increasing particle porosity. As indicated above, it is believed that generally spherical porous particles do not give the desired properties for the materials of the present invention. In accordance with an aspect of the present invention, it has been found, surprisingly, that the herein described, unconventional, spray drying of an amino acid gives particles having a new and particularly desirable morphology.

To give the best properties for the leucine and other amino acids produced by spray drying, it has been found that the droplet size is advantageously very small. The droplet size used in Pharmaceutica Acta Helvetiae 70(1995) 133–139 is at least 30 μm. Most advantageously, the droplets dried in the method of the present invention have a mean size of not more than 10 μm, more preferably, not more than 5 μm.

It is also believed that a high temperature for the spray drying is of importance. In many cases, the temperature of the spray drying for the formation of advantageous particles in accordance with at least one aspect of the present invention will be significantly greater than that used in conventional spray drying techniques. For example, the inlet air temperature of the spray dryer may be greater than 150° C., preferably greater than 200° C. at ambient pressure. The temperature of spray drying is of particular importance for materials which sublime and then condense to form the desired particle morphology. In such cases, advantageously the spray drying conditions are such that the desired sublimation takes place, at least of part of the material, in the spray drying.

For both the first and second aspects of the invention in respect of the method, advantageously the method is such that the MMAD of the solid amino acid particles produced is not more than 10 μm. As indicated above, amino acid particles having a small particle size can be used as an additive to improve the flow properties of powders.

Advantageously, the method is such that the amino acid particles produced are low-density amino acid particles as described above.

The invention also provides amino acid obtainable by a method as described above.

For ease of reference, the amino acid particles prepared by a method as described above will also be referred to as "low-density amino acid". Also, where the low-density amino acid comprises, for example, leucine, the material will be referred to a "low-density leucine". It should be appreciated, however, that the amino acid produced by the methods might not have, for example, the bulk density required in respect of the first aspect of the invention relating to the amino acid particles described above.

According to the invention, there is also provided a method of making a powder, the method including the steps of mixing low-density amino acid with active material.

As indicated above, the powder for may also include a diluent. In that case, advantageously, the method of producing the powder includes the step of mixing the low-density amino acid with active material followed by the step of mixing the low-density amino acid and active material with the diluent.

According to the invention, there is also provided the use of low-density amino acid in a powder to improve the flow properties of the powder.

Also provided is the use of low-density amino acid in a powder for use in a dry powder inhaler.

As indicated above, the use of the amino acid can improve the respirable fraction of the active material in the powder. It is thought that the respirable fraction is improved due to the improved dispersion of active material on actuation of the inhaler. Furthermore, where the powder also includes carrier particles, it is thought that the low-density amino acid promotes the release of the active particles from the surfaces of the carrier particles on actuation of the inhaler.

The active material referred to throughout the specification will be material comprising one or a mixture of pharmaceutical products. It will be understood that the term "active material" includes material that is biologically active, in the sense that it is able to decrease or increase the rate of a process in a biological environment. The pharmaceutical products include those products that are usually administered orally by inhalation for the treatment of disease such as respiratory disease, for example β-agonists, salbutamol and its salts or salmeteroli and its salts. Other pharmaceutical products which could be administered using a dry powder inhaler include peptides and polypeptides such as DNase, leucotrienes and insulin.

The active material may include a $\beta_2$-agonist, which may include salbutamol a salt of salbutamol or a combination thereof. Salbutamol and its salts are widely used in the treatment of respiratory disease. The active material may be salbutamol sulphate. The active material may be terbutaline, a salt of terbutaline, for example terbutaline sulphate, or a combination thereof. The active material may be ipatropium bromide.

The active material may include a steroid, which may be beclomethasone dipropionate or may be fluticasone. The active material may include a cromone, which may be sodium cromoglycate or nedocromil or its salts. The active material may include a leukotriene receptor antagonist.

The active material may include a carbohydrate, for example heparin.

Bulk Density

The bulk density (or poured density) of a material of the present invention is determined by the following method:

2 g of the material is poured from weighing paper into a 100 cm$^3$ graduated glass measuring cylinder in an upright position. Transfer of the material from the paper into the cylinder is made as rapidly as flow permits. The volume occupied by the poured powder in the cylinder is measured to the nearest 0.5 ml (bulk volume) and the weight of the powder is determined.

The bulk density of the material is calculated as the weight of the powder divided by the bulk volume.

An alternative method of measuring the bulk density is described in the European Pharmacopoeia 1997 2.9.15.

Particle Size Distribution

The particle size distribution was determined by low angle laser light scattering (Mastersizer X, Malvern Instruments, Malvern, UK). To approximately 5 mg of the sample to be analysed 10 ml of dispersant was added (0.05% lecithin in cyclohexane). The sample suspension was sonicated for 30 seconds before analysis. The volume median diameter (VMD) and D(v,90) were determined. VMD is the diameter such that 50% of the particles by volume have a diameter less than the VMD. D(v,90) is the equivalent volume diameter at 90% cumulative volume.

Mass Median Aerodynamic Diameter (MMAD)

The MMAD of particles of a material of the present invention is determined using Multi-Stage Liquid Impinger in accordance with the method described in European Pharmacopoeia (supplement 1999) 2.9.18. (Aerodynamic assessment of fine particles) for powder inhalers.

Embodiments for the invention will now be described by way of example.

EXAMPLE 1

Spray-dried leucine was prepared by the following method.

L-leucine was spray-dried using a laboratory scale co-current spray-dryer (Model 191, Büchi, Switzerland). A solution of 1.0% w/w L-leucine in water was prepared and atomised at a rate of 4.5 ml min$^{-1}$ using compressed air (600 l hr$^{-1}$, 0.7 mm nozzle). The droplets produced in the spray-dryer had a VMD of not more than about 10 μm. The inlet and outlet air temperatures of the spray dryer were 220° C. and 150° C. respectively.

The resulting powder was collected by cyclone separation transferred to glass vials and stored in a desiccator at room temperature over silica gel until used. The spray-dried L-leucine was a light, loose white powder. A microscopic examination of the spray-dried powder showed the presence of thin, flake-like particles.

The bulk density and particle size diameter (as VMD) were determined for the spray-dried leucine. Bulk density and VMD were determined by the method indicated above.

Table 1 shows the bulk density and particle size distribution for unprocessed L-leucine and for 5 batches of L-leucine spray-dried by the method of Example 1. It will be seen that the spray-dried leucine had bulk densities in the range 0.02 g cm$^{-3}$ to 0.05 g cm$^{-3}$.

TABLE 1

| Sample of L-leucine | Bulk Density (g cm$^{-3}$) | VMD (μm) | D(v,90)* |
|---|---|---|---|
| unprocessed | 0.710 | ND | ND |
| spray-dried A | 0.042 | 4.2 | 10.6 |
| spray-dried B | 0.035 | ND | ND |
| spray-dried C | 0.029 | ND | ND |
| spray-dried D | 0.035 | ND | ND |
| spray-dried E | 0.032 | 3.9 | 11.9 |

ND - Not Determined
*D(v,90) is the diameter below which 90% of particles by volume reside.

Flow Properties

The flow properties of the L-leucine were determined by measuring the Carr's Index of the powder. Spray-dried L-leucine was added to a powdered protein (BSA-maltodextrin 50:50).

Carr's Index of a sample was determined by measuring the volume ($V_{pour}$) of weight (W) poured into a 250 cm$^3$ measuring cylinder and tapping the cylinder to obtain constant volume of the sample ($V_{tap}$). The poured density (bulk density) and the tap density are calculated as $W/V_{pour}$ and $W/V_{tap}$ respectively and Carr's Index is calculated from the tapped density and the poured density by the formula $$\text{Carr's Index} \atop (\%) = \frac{\text{tapped} - \text{poured}}{\text{tapped}} \times 100$$

Table 2 shows the poured density (bulk density), tapped density and Carr's Index.

TABLE 2

| Sample | Poured Density (gcm$^{-3}$) | Tapped Density (gcm$^{-3}$) | Carr's Index (%) |
|---|---|---|---|
| unprocessed L-leucine | 0.710 | 0.770 | 8.5 |
| spray-dried L-leucine | 0.043 | 0.055 | 21.8 |
| BSA-maltodextrin (50:50) | 0.240 | 0.540 | 55.5 |
| BSA-maltodextrin (50:50) + spray-dried L-leucine | 0.093 | 0.146 | 36.0 |

The addition of the spray-dried leucine to the protein powder gives a lower Carr's Index indicating improved flow properties.

EXAMPLE 2

Aerosolised leucine was prepared by the following method.

Ground L-leucine was passed through a tube furnace. The L-leucine particles were suspended from a fluidised bed by a flow of air (about 20 l min$^{-1}$). The particles were carried in a gas flow into the tube furnace, which was at a temperature ranging from 150 to 300° C. The material sublimed. The vapour emitted from the furnace was mixed with cool air giving a cloud of condensed particles that were subsequently collected in a cyclone and membrane filter. The material collected was light and "fluffy" and includes particles in the form of thin flakes.

The bulk density and particle size distribution were determined by the methods described in respect of Example 1 above, and are given in Table 3.

TABLE 3

| Sample of L-leucine | Bulk Density (gcm$^{-3}$) |
|---|---|
| unprocessed | 0.70 |
| milled (VMD = 18 μm) | 0.30 |
| condensed | 0.04 |

Twin Stage Impinger

Powder blends were tested in a twin stage impinger (TSI) (European Pharmacopoeia 1997 2.9.18) to assess the efficiency of the delivery of the active particles to the lungs of a patient by an inhaler device.

The TSI is a two-stage separation device used in the assessment of oral inhalation devices. Stage one of the apparatus including the upper impinger is a simulation of the upper respiratory tract. Stage two which includes the lower impinger is a simulation of the lower respiratory tract. The liquid used in both the upper and lower impinger is distilled water for the examples below.

In use, the inhaler is placed in a mouth of the TSI. Air is caused to flow through the apparatus by means of a pump, which is connected to stage two of the TSI. Air is sucked through the apparatus from the mouth, flows through upper tubing via the upper impinger and the lower tubing to the lower impinger where it bubbles through liquid and exits the apparatus via outlet pipe. The liquid in the upper impinger traps any particle with a size such that it is unable to reach stage two of the TSI. Fine particles, which are the particles able to penetrate to the lungs in the respiratory tract, are able to pass into stage two of the TSI where they flow into the lower impinger liquid.

30 ml of distilled water is put into the lower impinger and 7 ml of distilled water is put into the upper impinger. The pump is adjusted to give an air flow rate of 60 liters per minute in the apparatus.

The inhaler device is weighed. The mouthpiece of the inhaler device is connected to the mouth of the TSI, the inhaler is actuated to dispense a dose of the powder and the pump is switched on and timed for a period of ten seconds. The pump is then switched off and the inhaler is removed from the TSI, re-weighed and the amount of powder lost from the inhaler calculated.

The sections of the apparatus making up stage one of the TSI are washed into a second flask and made up to 250 ml with distilled water. The sections making up the second stage of the TSI are washed into a third flask and made up to 100 ml with distilled water.

The amount of active substance in each section of the TSI is measured for each test. The following method may be used.

The contents of the flasks containing the washings from the stages of the TSI are assayed using High Performance Liquid Chromatography (HPLC) analysis for the content of the active material and compared against standard solutions containing, for example, 0.5 μg ml$^{-1}$ and 1 μg ml$^{-1}$ of the active material.

The percentage of the active material in each stage of the TSI is calculated from the standard response for each test and the mean for the tests may be calculated to give an indication of the proportion of the active particles reaching the second stage of the TSI apparatus. The respirable fraction (fine particle fraction) is calculated as the percentage of the total amount of drug emitted from the inhaler device that reaches stage two of the TSI and gives an indication of the proportion of active particles which would reach the deep lung in a patient.

Multi-Stage Liquid Impinger

Powder blends were also tested in a Multi-Stage Liquid Impinger (MSLI) (European Pharmacopoeia 2.9.18.) as indicated above to assess the efficiency of the delivery of the active particles to the lungs of a patient by an inhaler device.

The MSLI is a five-stage separation device used in the assessment of the fine particle characteristics of particle clouds generated using oral inhalation devices.

Impaction stage 1 is the pre-separator and stage 5 is an integral filter stage. An impaction stage comprises an upper horizontal metal partition wall through which a metal inlet jet tube with its impaction plate is protruding.

In use, a suitable low resistance filter capable of quantitatively collecting the active material is placed in stage 5. The apparatus is assembled and connected to a flow system. For the examples below, a flow rate of 90 liters per minute was used.

20 ml of a solvent is dispensed into each of stages 1 to 4. With the pump running, the mouthpiece of the inhaler device is located in the mouthpiece adapter of the MSLI and the inhaler device is discharged.

The amount of active ingredient in each stage of the apparatus is determined, for example using the method described in European Pharmacopoeia 2.9.18. Thus the fine particle dose can be calculated.

For the following examples, the inhaler device used in the TSI and MSLI tests was the Monohaler (manufactured by Miat, Italy).

EXAMPLE 3

Powder blends were produced for testing in the TSI apparatus. The blends were produced by a standard sequence of the following steps i. Mixing in a Turbula mixer (a tumbling blender) for between 30 minutes and 1 hour at fast speed;

ii. Passing the blend through a series of 600 μm, 420 μm and 355 μm aperture diameter sieves to improve mixing and to help break up stable agglomerates;

iii. Mixing the blend further in the Turbula mixer for between 30 minutes and 1 hour at a slow speed; and iv. Filling the blend into gelatine capsules for use in the Monohaler, each capsule containing about 5 mg of the blend.

Various powder blends were prepared comprising an active material, salbutamol sulphate, and an additive material. Several of the blends included low-density leucine in accordance with the invention as the additive material. The low-density leucine was prepared by an aerosol method as described in Example 2 above. Other blends included no additive material or Aerosil (trade name of Degussa for colloidal silicon dioxide) or conventional milled leucine as the additive material to give comparative results. The percentages given for the amount of additive material in the blend is the percentage by weight of the additive based on the weight of the active material and additive material.

The % given for the amount of components in the blends is the % by weight of the component based on the weight of the powder blend.

TABLE 4

| Sample | Mean mass of active material left in capsule (mg) | Mean respirable fraction (%) |
|---|---|---|
| Salbutamol | 3.7 | 27 |
| Salbutamol + 2% Aerosil | 1.7 | 75 |
| Salbutamol + 1% milled leucine | 2.3 | 14 |
| Salbutamol + 10% milled leucine | 2.3 | 13 |
| Salbutamol + 1% low-density leucine | 3.4 | 51 |
| Salbutamol + 10% low-density leucine | 2.3 | 31 |
| Salbutamol + 20% low-density leucine | 1.3 | 15 |

The table shows that the addition of the low-density leucine improved the respirable fraction of the active material. Particularly good results were obtained where the percentage by weight of the low-density leucine was 1%.

Micronised salbutamol powder itself is difficult to handle, being cohesive and adhesive and significantly affected by static. The powder forms hard compact agglomerates and sticks to or jumps from surfaces due to electrostatic forces. The addition of 1% and 10% by weight of milled leucine improved the powder flow and handling performance of the salbutamol powder. The mixes including 1% and 10% by weight of the low-density leucine had significantly improved powder flow characteristics, with minimal adhesion to glass walls compared with the milled leucine mixes.

EXAMPLE 4

The effect of the proportion of low-density leucine in the powder blend was determined by testing blends containing salbutamol sulphate and various percent by weight of low-density leucine. The effect of the method of blending was also investigated by combining the following mixing methods:

HS—high shear mixing using a food processor having a metal blade
LS—low shear mixing using a pestle and mortar and sieving
S—sieving
T—mixing in a tumbling blender (Turbula mixer)

The blends were tested using the TSI. The dose in each capsule of the powder blend was about 5 mg. Each test was repeated with a total of two capsules (a total of 10 mg of powder blend). The results are shown in Table 5.

The % given for the amount of components in the blends is the % by weight of the component based on the weight of the powder blend.

TABLE 5

| % by weight of low-density leucine | Mixing protocol | Mean mass of drug left in capsule (mg) | Mean respirable fraction (%) |
|---|---|---|---|
| None | — | 3.7 | 27 |
| 1.0 | HS | 4.7 | 56 |
| 1.0 | HS, S, T | 3.6 | 60 |
| 1.0 | LS, S, T | 4.0 | 69 |
| 2.5 | LS, S, T | 3.7 | 64 |
| 5.0 | LS | 4.4 | 59 |
| 5.0 | LS, S, T | 3.6 | 66 |
| 7.5 | LS | 3.6 | 60 |
| 7.5 | LS, S, T | 3.2 | 73 |

Thus it can be seen that the addition of low-density leucine gave a significant increase in the respirable fraction of the active material although, in each case, a large proportion of the active material remains in the device on actuation of the inhaler.

Salbutamol sulphate micronised powder is less difficult to handle than the salbutamol base powder but does exhibit cohesive and adhesive nature. While the addition of leucine gave some improvement in the powder flow and handling performance, the addition of the low-density leucine gave significantly improved powder flow and handling characteristics.

EXAMPLE 5

Powder blends for inhalation comprising active material, low-density leucine and lactose diluent were tested using a multi-stage liquid impinger (MSLI) using a flow rate of 90 liters per minute. The blends were prepared by mixing the active material and low-density leucine using the method described in respect of Example 3 above. The active material used was salbutamol sulphate and the low-density leucine was prepared by aerosolisation as described in Example 2 above. The mixture was then mixed with lactose. Two grades of lactose were used. Sorbolac (400) comprises lactose fines having an effective particle diameter of 7 $\mu$m and Lactochem comprises lactose having a particle size between 63 $\mu$m and 90 $\mu$m obtained by sieving. Capsules for testing were filled with between 20 mg and 25 mg of the powder blend.

The results of the MSLI tests are shown in Table 6. The % shown are the % by weight of the material based on the weight of the powder blend.

TABLE 6

| % of low-density leucine | % of lactose and grade | Active material left in the device (%) | Respirable fraction (%) |
|---|---|---|---|
| 1.0 | 50 Sorbolac | 21 | 65 |
| 7.5 | 90 Lactochem | 11 | 55 |
| 7.5 | 90 Sorbolac | 14 | 59 |

Thus it can be seen that the high respirable fraction is maintained on the inclusion of the lactose but the emptying of the capsule in improved compared with the blends which do not contain the lactose.

The use of the low-density leucine material has been described above in relation to its use in powders for pharmaceutical use, in particular in powders for inhalation for which the powder properties are of great importance.

The low-density amino acid of the present invention may also be used in other pharmaceutical applications. The low-density leucine may be used, for example, in powder formulations for tabletting. The advantageous properties, in particular the flow properties, would improve the performance of the powder in the pressing of tablets.

The low-density amino acid may also be used as an additive in powders to be filled into capsules. The improved flow and handling characteristics of the powders containing the low-density amino acid would give improved filling and emptying of the capsules.

There are several additive materials currently available and which are routinely added to powders to improve their flow properties, for example Aerosil (colloidal silica). A significant advantage of amino acids compared with, for example, silica is that amino acids are more pharmaceutically acceptable, in particular for inhalation into the lung.

A further advantage of some amino acids, in particular leucine, over silica is that, unlike silica, leucine dissolves in water to give a clear solution. It is envisaged, therefore, that the low-density amino acid, for example leucine, could advantageously be used in powders for use as diagnostic reagents for which the ability to form a clear solution may be essential.

It also envisaged that the low-density amino acids may find application in fields other than pharmaceutical field. For example, the low-density amino acid may be used in dry powders for fire suppressants, for example to improve the powder properties of powders in dry powder fire extinguishers.

We claim:

1. Amino acid particles, in which the particles have a bulk density not more than 0.1 $gcm^{-3}$.

2. Amino acid particles according to claim 1, in which the particles have a bulk density not more than 0.05 $gcm^{-3}$.

3. Amino acid particles having a mass median aerodynamic diameter (MMAD) not more than 5 $\mu$m.

4. Amino acid particles being in the form of flakes having a thickness of not more than 0.5 $\mu$m.

5. Amino acid particles according to claim 4 in which the flakes having a thickness of not more than 100 nm.

6. Amino acid particles according to claim 1, in which the amino acid is leucine.

7. A powder for use in a dry powder inhaler, the powder including active material and amino acid particles according to claim 1.

8. A powder according to claim 7, in which the powder includes not more than 20% by weight of amino acid based on the weight of the powder.

9. A powder according to claim 8, in which the powder includes not more than 10% by weight of amino acid based on the weight of the powder.

10. A powder for use in a dry powder inhaler, said powder including active material, particles of a diluent, and amino acid particles in which the amino acid particles have a bulk density of not more than 0.1 $gcm^{-3}$.

11. A powder according to claim 10, in which the diluent includes a crystalline sugar.

12. A powder according to claim 10, in which the diluent has a particle size such that at least 90% by weight of the diluent particles have a particle size not more than 10 $\mu$m.

13. A powder according to claim 10, in which the diluent has a particle size such that at least 90% by weight of the diluent particles have a particle size not less than 50 $\mu$m.

14. A powder according to claim 10, in which the diluent has a fine particle portion having a particle size such that at least 90% by weight of the particles of the fine particle portion have a particle size not more than 10 $\mu$m and a coarse particle portion having a particle size such that at least 90% by weight of the particles of the coarse particle portion have a particle size not less than 50 $\mu$m.

15. A powder according to claim 14, in which the fine particle portion and coarse particle portion comprise the same material.

16. A powder according to claim 14, in which the powder includes not more than 5% by weight of the fine particle portion based on the weight of the powder.

17. A powder according to claim 14, in which the powder includes not more than 95% by weight of the coarse particle portion based on the weight of the powder.

18. A dry powder inhaler, the inhaler containing powder, wherein said powder includes active material and amino acid particles in which the amino acid particles have a bulk density of not more than 0.1 $gcm^{-3}$.

19. A method of preparing particles of amino acid, the method including the step of forming solid amino acid particles from a vapor or from a solvent, the method being such that the particles are formed while being suspended in a gas flow, said particles having a mass median aerodynamic diameter (MMAD) not more than 5 $\mu$m.

20. A method of preparing particles of amino acid, the method including the step of condensing amino acid vapor to form solid amino acid particles, wherein said amino acid particles have a bulk density not more than 0.1 $gcm^{-3}$.

21. A method according to claim 19, in which particles of amino acid are formed by aerosol condensation.

22. A method according to claim 20, in which the method includes the steps of
 a) heating the amino acid so that the amino acid forms a vapor;
 b) mixing the amino acid vapor with cool air to form a cloud of condensed amino acid particles; and
 c) collecting the condensed particles.

23. A method according to claim 20, the method including the step of heating the amino acid particles to a temperature of at least 150° C. at ambient pressure.

24. A method according to claim 19, in which the method includes the step of spray drying to form solid particles of amino acid.

25. A method according to claim 24, in which the material to be dried comprises amino acid in solution.

26. A method according to claim 19, in which the method is such that the MMAD of the solid amino acid particles produced is not more than 10 $\mu$m.

* * * * *